United States Patent
Remboski et al.

(10) Patent No.: US 12,339,243 B2
(45) Date of Patent: Jun. 24, 2025

(54) OIL LUBRICANT QUALITY SENSOR FOR A LUBRICANT SUPPORTED ELECTRIC MOTOR AND AN OIL COOLED INVERTER

(71) Applicant: Neapco Intellectual Property Holdings, LLC, Farmington Hills, MI (US)

(72) Inventors: Donald James Remboski, Ann Arbor, MI (US); Patrick A. O'Gorman, Escondido, CA (US); Gorazd Gotovac, Ljubljana (SI)

(73) Assignee: Neapco Intellectual Property Holdings, LLC

( * ) Notice: Subject to any disclaimer, the term of this patent is extended or adjusted under 35 U.S.C. 154(b) by 343 days.

(21) Appl. No.: 17/975,166

(22) Filed: Oct. 27, 2022

(65) Prior Publication Data
US 2023/0134353 A1 May 4, 2023

Related U.S. Application Data

(60) Provisional application No. 63/273,295, filed on Oct. 29, 2021.

(51) Int. Cl.
*G01N 27/02* (2006.01)
*F01M 11/10* (2006.01)
(Continued)

(52) U.S. Cl.
CPC ........... *G01N 27/026* (2013.01); *F01M 11/10* (2013.01); *F16N 29/00* (2013.01);
(Continued)

(58) Field of Classification Search
CPC ............. G01N 27/026; G01N 33/2847; G01N 33/2858; G01N 33/2888; F01M 11/10;
(Continued)

(56) References Cited

U.S. PATENT DOCUMENTS

2007/0151806 A1* 7/2007 Boyle ................ G01N 33/2888
184/6.21
2013/0342150 A1* 12/2013 Ozaki ................ F16H 57/0476
318/490

(Continued)

FOREIGN PATENT DOCUMENTS

JP 2015027820 A 2/2015
WO WO-2013118703 A1 * 8/2013 ............. H02K 11/33

OTHER PUBLICATIONS

English Machine Translation of WO 2013/118703 A1 (Year: 2013).*

*Primary Examiner* — David Z Huang
(74) *Attorney, Agent, or Firm* — Dickinson Wright PLLC (57) ABSTRACT

A quality diagnostics system for lubricant/coolant fluid includes a lubricant supported electric motor including a stator and a rotor defining a gap therebetween, with the lubricant/coolant fluid disposed in the gap for supporting the rotor while allowing the rotor to rotate relative to the stator. An inverter includes a plurality of power switches configured to supply an alternating current (AC) power to the motor for driving the rotor to rotate. A passageway conveys the lubricant/coolant fluid between the motor and the inverter. A lubricant quality sensor includes a set of sensor plates disposed along the passageway, an excitation source configured to apply an AC excitation voltage to a first sensor plate, and an electrical sensor configured to measure a response to the AC excitation voltage. A controller determines, based on a sensor signal from the electrical sensor, at least one of metal contamination and water contamination in the lubricant/coolant fluid.

18 Claims, 5 Drawing Sheets

(51) Int. Cl.
  *F16N 29/00* (2006.01)
  *G01N 33/28* (2006.01)
  *H02K 5/20* (2006.01)
  *H02K 9/19* (2006.01)
  *H02K 11/33* (2016.01)
  *H02K 11/35* (2016.01)

(52) U.S. Cl.
  CPC ..... *G01N 33/2847* (2013.01); *G01N 33/2858* (2013.01); *G01N 33/2888* (2013.01); *H02K 5/203* (2021.01); *H02K 9/19* (2013.01); *H02K 11/33* (2016.01); *H02K 11/35* (2016.01); *F01M 2011/1473* (2013.01); *F16N 2200/04* (2013.01); *F16N 2200/10* (2013.01); *F16N 2200/18* (2013.01); *F16N 2200/20* (2013.01); *H02K 2211/03* (2013.01)

(58) Field of Classification Search
  CPC .......... F16N 29/00; H02K 5/203; H02K 9/19; H02K 11/35
  See application file for complete search history.

(56) References Cited

U.S. PATENT DOCUMENTS

| | | | |
|---|---|---|---|
| 2020/0130408 A1* | 4/2020 | Remboski | H02K 7/006 |
| 2021/0088124 A1 | 3/2021 | Remboski et al. | |
| 2021/0211069 A1 | 7/2021 | Reed et al. | |

* cited by examiner

OIL LUBRICANT QUALITY SENSOR FOR A LUBRICANT SUPPORTED ELECTRIC MOTOR AND AN OIL COOLED INVERTER

CROSS-REFERENCE TO RELATED APPLICATIONS

This utility application claims the benefit of U.S. Provisional Application No. 63/273,295 filed Oct. 29, 2021. The entire disclosure of the above application is incorporated herein by reference.

FIELD OF THE DISCLOSURE

The present disclosure relates generally to a lubricant supported electric motor and an oil cooled inverter. More specifically, the present disclosure relates to oil quality diagnostics used in association with a lubricant supported electric motor and an oil cooled inverter which share a common lubricating and cooling fluid.

BACKGROUND OF THE INVENTION

This section provides a general summary of background information and the comments and examples provided in this section are not necessarily prior art to the present disclosure.

Various drivelines in automotive, truck and certain off-highway applications take power from a central prime mover and distribute the power to the wheels using mechanical devices such as transmissions, transaxles, propeller shafts, and live axles. These configurations work well when the prime mover can be bulky or heavy, such as, for example, various internal combustion engines ("ICE"). However, more attention is being directed towards alternative arrangements of prime movers that provide improved environmental performance, eliminate mechanical driveline components, and result in a lighter-weight vehicle with more space for passengers and payload.

"On wheel", "in-wheel" or "near-wheel" motor configurations are one alternative arrangement for the traditional ICE prime mover that distributes the prime mover function to each or some of the plurality of wheels via one or more motors disposed on, within, or proximate to the plurality of wheels. For example, in one instance, a traction motor, using a central shaft though a rotor and rolling element bearings to support the rotor, can be utilized as the "on wheel", "in wheel" or "near wheel" motor configuration. In another instance, a lubricant supported electric motor can be utilized as the "on wheel", "in wheel" or "near wheel" motor configuration. While each of these motor configurations result in a smaller size and lighter weight arrangement as compared to the prime movers based on the internal combustion engine, they each have certain drawbacks and disadvantages.

One aspect of electric drive motors that adds to their cost and complexity is the requirement for a variety of fluids used for different functions of the electric drive motor and associated systems. For example, a wheel end electric system often includes a water-glycol cooling fluid for the electric motor and separate cooling fluids for other components (e.g., the inverter, gearing, bearings, and hydraulic brakes) of the electric drive system. Each of these fluids require separate storage compartments and distribution channels, as well as systems for distributing or cycling the fluids to the desired locations within the systems. In the water-glycol cooled traction motors, the cooling fluid also does not touch the moving motor parts, such as the bearing surfaces, and thus cannot cool these components and is unable to support the rotor relative to the stator, such as is the case with lubricant supported electric motors. In addition, fluid passages defined by the electric motor are not narrow enough to block the flow of the coolant.

Additionally, water-based coolants must be separated from hydrocarbon lubricated surfaces and from high voltage and low voltage electronics. A water-glycol based coolant coming into contact with electronics can lead to electrical shorts and substantial damage to the electrical components. Thus, using water-glycol coolants to cool electronics requires the use of heat exchangers, which are themselves costly, bulky and heavy. Accordingly, most inverters require that the electronic components are separated by an aluminum plate from the coolant fluid, so that the fluid is never in contact with the power components. For these reasons, a water-glycol fluid is not a suitable a candidate for a shared lubricant and cooling system which utilizes the same fluid to lubricate and cool the electric motor and electric components, such as the inverter. However, it is recognized that a motor may be cooled using a hydrocarbon lubricant which is then connected to heat exchanger wherein the heat from the hydrocarbon lubricant is rejected to a water-glycol coolant loop, which may or may not also cool the electronics.

It is also a requirement of the prior art systems to detect for major contaminants (e.g., metal particles and water) in the lubricants or coolants which if contaminated can reduce the life of the lubricant/coolant and lead to premature failure of the motor and/or the electric components, such as the inverter. Foaming is not a contaminant, but it can starve the pump resulting in reduced fluid flow and possible motor or inverter failure. Thus it is also desirable to detect this foaming condition and take appropriate action to mitigate its presence.

Sensors are often used in internal combustion engines ("ICEs") to detect for the presence of major contaminants in the oil. However, the presence of contaminants in engine oil is mitigated through regular maintenance of the internal combustion engines, namely the changing of engine oil on regular intervals (e.g., every 3,000 to 5,000 miles) which necessarily results in the disposal of any contaminated oil on a regular basis. However, in contradistinction to ICEs, lubricant supported electric motors are preferably designed such that the lubricant is never changed for the life of the electric vehicle. Furthermore, with ICEs, the presence of small quantities of water in the oil is removed through boiling from contract with engine surfaces having temperatures in excess of the boiling point of water. However, these ICE surface temperatures are far in excess of the maximum temperatures experienced in an electric vehicle drive application. Thus, the need to remove major contaminants (oil and water) is a more significant problem in lubricant supported electric motors compared to their ICE counterparts.

The limited number of prior art lubricant cooled electric motors often utilize a standard oil filter to separate out metal particles, but do not have any mitigation against water ingress into the lubricant. Furthermore, most elective vehicle drivetrains are water/glycol cooled, and thus the concern with the presence water in the lubricant does not typically arise. Thus, there remains a continuing need for improved diagnostics for detecting the presence of both metal and water in a shared fluid used for both a lubricant supported electric motor as well as to cool electric components, such as an inverter.

SUMMARY OF THE INVENTION

The present disclosure provides a quality diagnostics system for lubricant/coolant fluid. The system includes a lubricant supported electric motor including a stator and a rotor defining a gap therebetween, with the lubricant/coolant fluid disposed in the gap for supporting the rotor while allowing the rotor to rotate relative to the stator. The system also includes an inverter including a plurality of power switches configured to supply an alternating current (AC) power to the lubricant supported electric motor for driving the rotor to rotate. The system also includes a passageway configured to convey the lubricant/coolant fluid between the lubricant supported electric motor and the inverter. The system also includes a lubricant quality sensor including a set of sensor plates disposed along the passageway, an excitation source configured to apply an AC excitation voltage to a first sensor plate of the set of sensor plates, and an electrical sensor configured to measure a response to the AC excitation voltage. It should be noted that while the operation of a single sensor is described in this disclosure, it may be advantageous to deploy more than one sensor in the system. It is further noted that the configuration of multiple sensors is not necessarily the same, as it may be advantageous to change the separation between the plates or the surface area of the plates, to enhance the ability to detect various contaminants.

The present disclosure also provides a quality diagnostics system for lubricant/coolant fluid of a vehicle. The system includes a lubricant supported electric motor including a stator and a rotor defining a gap therebetween, with a lubricant/coolant fluid disposed in the gap for supporting the rotor while allowing the rotor to rotate relative to the stator. The system also includes a passageway configured to convey the lubricant/coolant fluid between the lubricant supported electric motor and one or more other components. The system also includes a lubricant quality sensor including a set of sensor plates disposed along the passageway and an excitation source configured to supply an AC excitation voltage to at least one sensor plate of the set of sensor plates. The system also includes a controller configured to cause the excitation source to apply the AC excitation voltage to the at least one sensor plate. The system also includes an electrical sensor configured to measure an electrical response to the application of the AC excitation voltage. The controller is further configured to determine, based on a sensor signal from the electrical sensor, at least one of metal contamination and water contamination in the lubricant/coolant fluid.

The present disclosure also provides a method for sensing contaminants in a lubricant/coolant fluid of a lubricant supported electric motor. The method includes: circulating the lubricant/coolant fluid through a passageway and to the lubricant supported electric motor; applying, by an excitation source, an AC excitation voltage to a first sensor plate disposed adjacent to and along the passageway; sensing, by an electrical sensor, a response to the application of the AC excitation voltage; and determining, based on the response to the application of the AC excitation voltage, at least one of metal contamination and water contamination in the lubricant/coolant fluid. It should be noted that the detection of contaminants in the overall lubricant/cooling fluid may occur outside the motor enclosure itself. It may be advantageous to place a circuit board with the necessary plate configurations somewhere in the oil flow path to determine if contaminants exist in the lubricant/coolant fluid.

BRIEF DESCRIPTION OF THE DRAWINGS

The drawings described herein are for illustrative purposes only of selected embodiments and not all possible implementations, and are not intended to limit the scope of the present disclosure.

DETAILED DESCRIPTION OF THE ENABLING EMBODIMENTS

Example embodiments of a common lubrication, cooling and quality diagnostics system 10 for electric powertrains that include lubricant supported electric motors and inverters will now be more fully described. Each of these example embodiments are provided so that this disclosure is thorough and fully conveys the scope of the inventive concepts, features and advantages to those skilled in the art. To this end, numerous specific details are set forth such as examples of specific components, devices and mechanisms associated with the lubricant supported electric motor to provide a thorough understanding of each of the embodiments associated with the present disclosure. However, as will be apparent to those skilled in the art, not all specific details described herein need to be employed, the example embodiments may be embodied in many different forms, and thus should not be construed or interpreted to limit the scope of the disclosure.

The use of a shared lubricant/coolant fluid system including a common lubricant quality sensor improves contamination detection, while also reducing the overall size, weight, and volume of the system relative to a system requiring the use of different lubricant fluids for different applications. The lubricant quality sensor of the present disclosure also improves on prior art contamination detection mechanisms that are only able to reliably detect for the presence of oil or water, but not both.

The present disclosure provides a lubricant supported electric motor and an electric component, such as an inverter, having a shared lubricating and cooling system. More specifically, the system uses a common lubricant/coolant fluid that is both disposed within a lubricant supported electric motor to lubricant the electric motor and support the rotor relative to the stator, while also being used to cool electronic modules of the system, such as the inverter. The lubricant is preferably a dielectric oil such that the lubricant can be introduced directly into the inverter such that it is able to make direct contact with its components, while also serving to lubricate and support the rotor of the lubricant supported electric motor. A lubricant quality sensor is disposed in communication with the common lubricant/ coolant fluid to detect for both the presence of metal and water contamination within the common lubricant/coolant fluid system.

Figure 1:
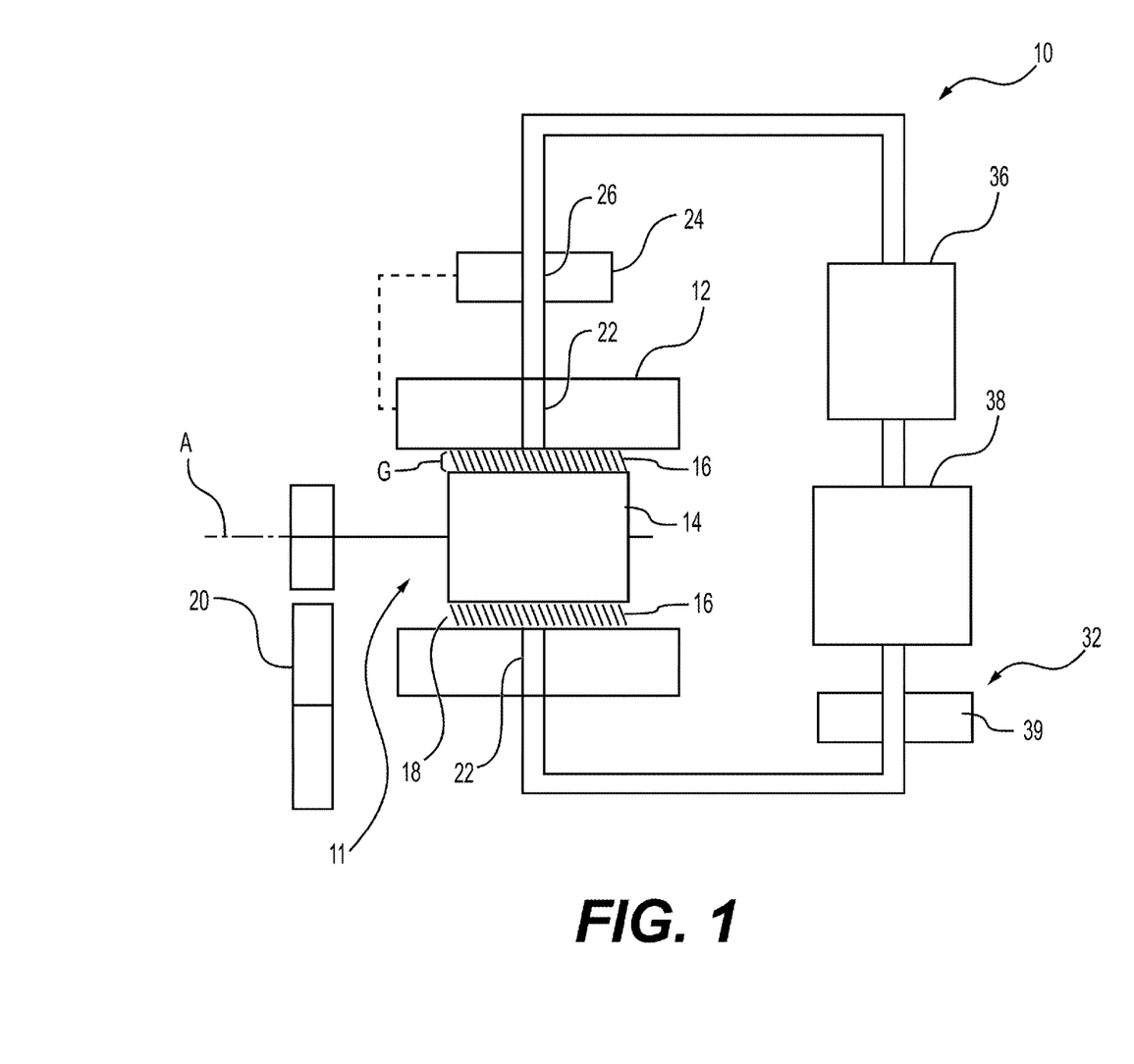
FIG. 1 shows a schematic view of a system including a lubricant supported electric motor and an inverter having a coolant/lubricant fluid, in accordance with an aspect subject disclosure.

FIG. 1 illustrates a common lubrication, cooling and quality diagnostics system 10 for a lubricant supported electric motor 11 of the disclosure. As best illustrated in FIG. 1, the lubricant supported electric motor 11 includes a stator 12 and a rotor 14 extending along an axis A and movably disposed within the stator 12 to define a support chamber 16 or gap G therebetween. Although illustrated and described with the rotor 14 disposed within the stator 12, the arrangement of these components can also be reversed (i.e., with the rotor 14 disposed in surrounding relationship with the stator 12) without departing from the scope of the subject disclosure. A lubricant/coolant fluid 18 is disposed in the support chamber 16 for supporting the rotor 14 within and relative to the stator 12, allowing the rotor 14 to rotate relative to the stator 12 and lubricating and cooling these components. The lubricant/coolant fluid 18 acts as a buffer (e.g., suspension) between the rotor 14 and stator 12 minimizing or preventing contact therebetween. In other words, the lubricant/coolant fluid 18 prevents direct contact between the stator 12 and rotor 14 and provides a lubricant supported electric motor 11 which is robust to shock and vibration loading due to the presence of the lubricant/coolant fluid 18 in the support chamber 16. Additionally, and alternatively, a lubricant/coolant fluid that is substantially incompressible may be used in order to minimize the gap between the stator 12 and rotor 14.

As further illustrated in FIG. 1, the rotor 14 is interconnected to a drive assembly 20 for coupling the lubricant supported electric motor 11 to one of the plurality of wheels of a vehicle. For example, in one instance, the drive assembly 20 may include a planetary gear system. Alternatively, the drive assembly 20 may include one or more parallel axis gears. In either arrangement, the lubricant supported electric motor 11 is arranged in an "on-wheel", "near-wheel" or "in-wheel" motor system in which the lubricant supported electric motor 11 is disposed proximate to, on, or within the vehicle wheel. Although not expressly illustrated, accordingly to another aspect, the lubricant supported electric motor 11 can be connected directly to the vehicle wheel, without the use of this drive assembly 20 to establish the "on-wheel", "near-wheel" or "in-wheel" electric motor arrangement. In any arrangement, the stator 12 and rotor 14 are configured to exert an electromagnetic force therebetween to convert electrical energy into mechanical energy, moving the rotor 14 and ultimately driving the wheel coupled to the lubricant supported electric motor 11. If present, the drive assembly 20 may provide one or more reduction ratios between the lubricant supported electric motor 11 and the wheel in response to movement of the rotor 14.

As further illustrated FIG. 1, the stator 12 defines a motor passageway 22 disposed in fluid communication with the support chamber 16 for introducing the lubricant/coolant fluid 18. However, the motor passageway 22 could be provided on any other components of the lubricant supported electric motor 11, without departing from the subject disclosure. An inverter 24 is disposed in electrical communication with the lubricant supported electric motor 11 and defines an inverter passageway 26 disposed in fluid communication with the motor passageway 22 for allowing the lubricant/coolant fluid 18 to also pass through the inverter 24 and over its electronic components. Thus, the lubricant/coolant fluid 18 used to lubricate and cool the lubricant supported electric motor 11 is also used for cooling the inverter 24. The lubricant/coolant fluid 18 may be a dielectric oil having a composition that acts as an electrical insulator, such that the lubricant/coolant fluid 18 will not conduct electricity, making the lubricant/coolant fluid 18 suitable for direct contact with electric components of the inverter 24. The dielectric oil also has good heat transfer properties, such that it may act well as a coolant for both the lubricant supported electric motor 11 as well as the inverter 24. The dielectric oil is also incompressible, making it a good candidate for supporting the rotor 14 relative to the stator 12 in the lubricant supported electric motor 11. Finally, the dielectric oil also serves as a good lubricant for use within the lubricant supported electric motor 11. The inverter 24 includes a number of electric components necessary to convert DC current into AC current, such as switches, transistors, semiconductors and the like.

As illustrated in FIG. 1, the lubricant/coolant fluid 18 is cycled or pumped through both the motor passageway 22 and the inverter passageway 26, and into their respective components, as one continuous fluid communication line. For example, a pump 36 may be fluidly coupled to a sump or reservoir 38 of the lubricant/coolant fluid 18, such that the lubricant/coolant fluid 18 is pumped from the reservoir 38, through the inverter passageways 26 and then into the motor passageways 22 and through the support chamber 16 of the lubricant supported electric motor 11. Alternatively, the lubricant/coolant fluid 18 may flow first through the lubricant supported electric motor 11 and then through the inverter passageways 26. In an alternative arrangement, rotation of the rotor 14 relative to the stator 12 could act as a self-pump to pull the lubricant/coolant fluid 18 through the passageways 22, 26 and into the support chamber 16. Although not expressly illustrated, a further enhancement of the system 10 includes that the reservoir 38 is designed with a low point where water present in the lubricant/coolant fluid 18 could collect. A diagnostic message to a driver of the vehicle could be sent indicating that a drain plug of the reservoir 38 needs to be opened to purge the tank of water.

Figure 2:
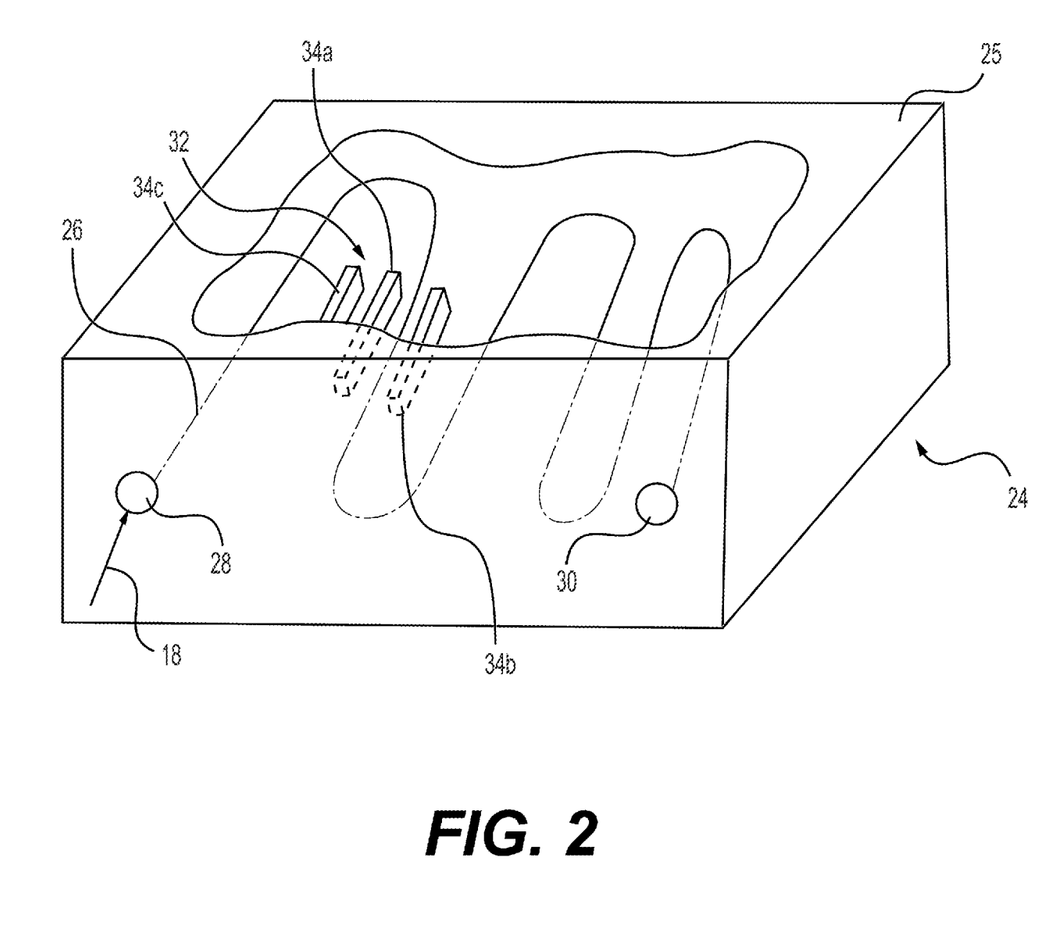
FIG. 2 shows a partial cut-away perspective view of the inverter of the present disclosure, illustrating a fluid passage for conveying the coolant/lubricant fluid therethrough.

With reference to FIG. 2, the inverter 24 includes an enclosure 25 that defines a fluid inlet 28 and a fluid outlet 30 such that the inverter passageway 26 flows between the fluid inlet 28 and the fluid outlet 30, allowing the lubricant/coolant fluid 18 to make direct contact with and flow over these electric components dispersed throughout the inverter 24. However, metal contaminants in the lubricant/coolant fluid 18 passing through the inverter passageway 26 could cause a short circuit between adjacent conductors, such as positive and negative device terminals of electric components within the inverter 24. This could result in failure of the inverter 24, which may require replacement of the inverter 24.

Accordingly, as further illustrated in FIG. 2, the inverter 24 includes a lubricant quality sensor 32 for detecting for the presence of both water and metal contamination in the lubricant/coolant fluid 18 that is passing through the inverter 24 as well as the lubricant supported electric motor 11. As will be appreciated in view of the following more detailed disclosure, the use of a lubricant quality sensor 32 to detect for major contaminants in the lubricant/coolant fluid 18 used by both the inverter 24 as well as the lubricant supported electric motor 11 improves on the prior art systems that require separate detection mechanisms dedicated to each of these components.

As further illustrated in FIG. 2, the lubricant quality sensor 32 includes a sensor on the power board, which consists of a set of sensor plates 34a, 34b disposed along and on opposite sides of the inverter passageway 26.

Figure 3:
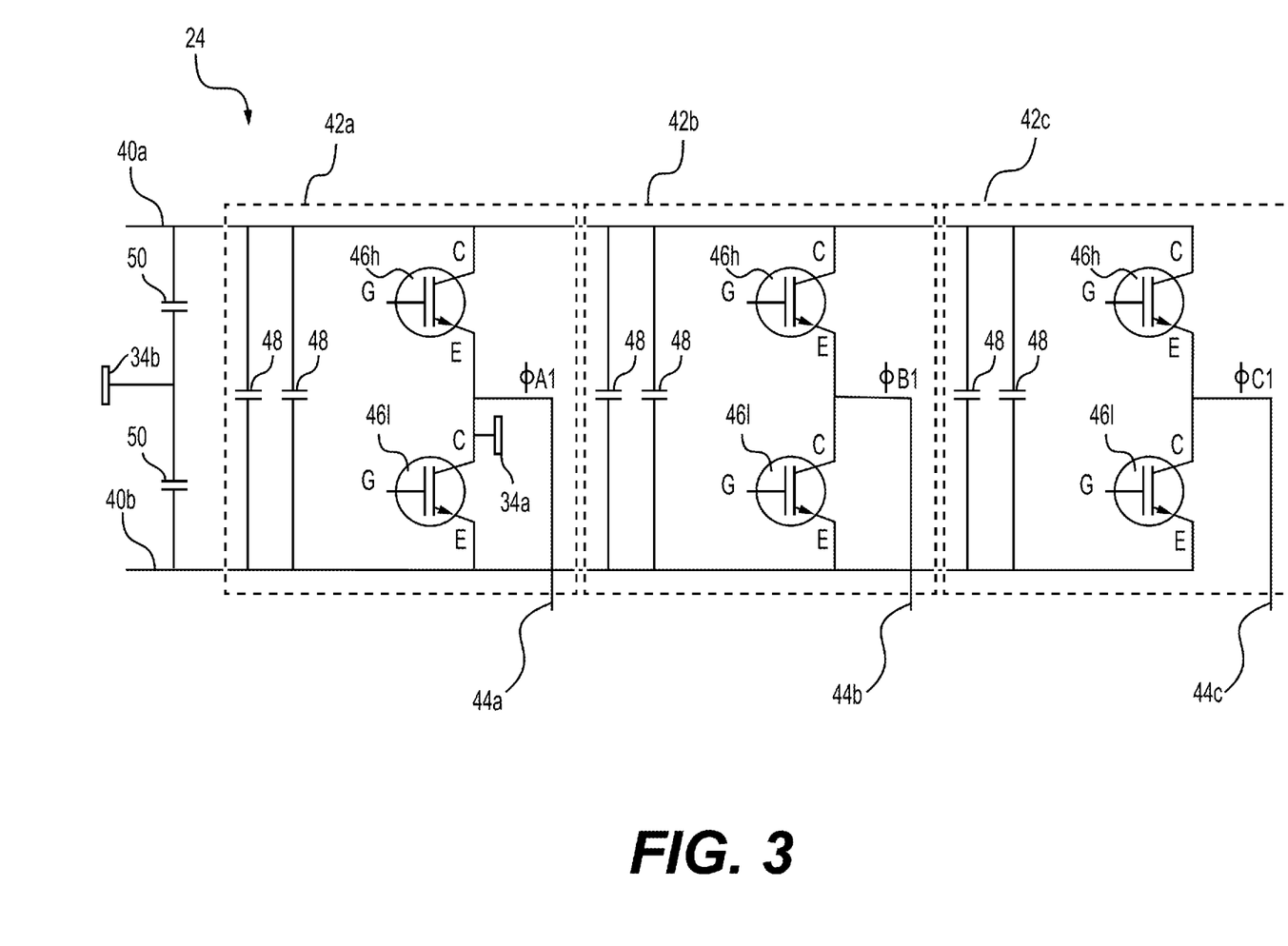
FIG. 3 shows an electrical schematic diagram showing a portion of the inverter in accordance with an aspect of the present disclosure.

FIG. 3 shows an electrical schematic diagram of a portion of the inverter 24. The inverter 24 includes a DC positive conductor 40a and a DC negative conductor 40b having a DC voltage therebetween. The inverter 24 includes an A-phase driver 42a configured to generate an alternating current (AC) power on an A-phase motor lead 44a for supplying current to a corresponding winding of the lubricant supported electric motor 11. The inverter 24 also includes a B-phase driver 42b configured to generate AC power on a B-phase motor lead 44b for supplying current to a corresponding winding of the lubricant supported electric motor 11. The inverter 24 also includes a C-phase driver 42c configured to generate AC power on a C-phase motor lead 44c for supplying current to a corresponding winding of the lubricant supported electric motor 11. Each of the phase drivers 42a, 42b, 42c includes a high-side power switch 46h configured to selectively conduct current between the DC positive conductor 40a and a corresponding one of the motor leads 44a, 44b, 44c. Each of the phase drivers 42a, 42b, 42c also includes a low-side power switch 46l configured to selectively conduct current between the DC negative conductor 40b and a corresponding one of the motor leads 44a, 44b, 44c. Each of the power switches 46h, 46l is shown schematically as a single insulated gate bipolar transistor (IGBT). However, other types of power switching devices may be used, such as field-effect transistors (FETs) or other types of junction devices. In some embodiments, one or more of the power switches 46h, 46l may include a parallel-connected combination of two or more discrete devices, such as IGBT devices. The inverter 24 is illustratively shown as a three-phase device having three of the phase drivers 42a, 42b, 42c. However, the principles of the present disclosure may be applied to other types of poly-phase systems, such as where the inverter 24 and the lubricant supported electric motor 11 are each six, nine, or twelve-phase devices.

Each of the phase drivers 42a, 42b, 42c also includes two DC link capacitors 48 connected between the DC positive conductor 40a and the DC negative conductor 40b adjacent to the switches 46h, 46l to supply relatively large inrush currents to the switches 46h, 46l and to reduce electromagnetic interference (EMI). A set of two input capacitors 50 are connected in series between the between the DC positive conductor 40a and the DC negative conductor 40b.

An excitation source applies an AC excitation voltage to a first plate 34a of the set of sensor plates 34a, 34b. In some embodiments, the inverter 24 function as the excitation source. For example, and as shown in FIG. 3, the first plate 34a may be connected to the A-phase motor lead 44a. However, the first plate 34a could be connected to any one of the motor leads 44a, 44b, 44c. The first plate 34a may also be called an excitation plate because of its configuration to have an AC excitation voltage applied thereto. A second plate 34b of the set of sensor plates 34a, 34b is connected to a midpoint node between the two input capacitors 50. The series combination of the two input capacitors 50 may maintain the second plate 34b at a steady DC voltage that is mid-way between the voltages of the DC positive conductor 40a and the DC negative conductor 40b. The second plate 34b may also be called a reference plate because of its steady or reference voltage. Alternatively, another power source, such as a dedicated AC source independent of the inverter 24, may function as the excitation source for applying the AC excitation voltage to the first plate 34a of the set of sensor plates 34a, 34b.

Figure 4:
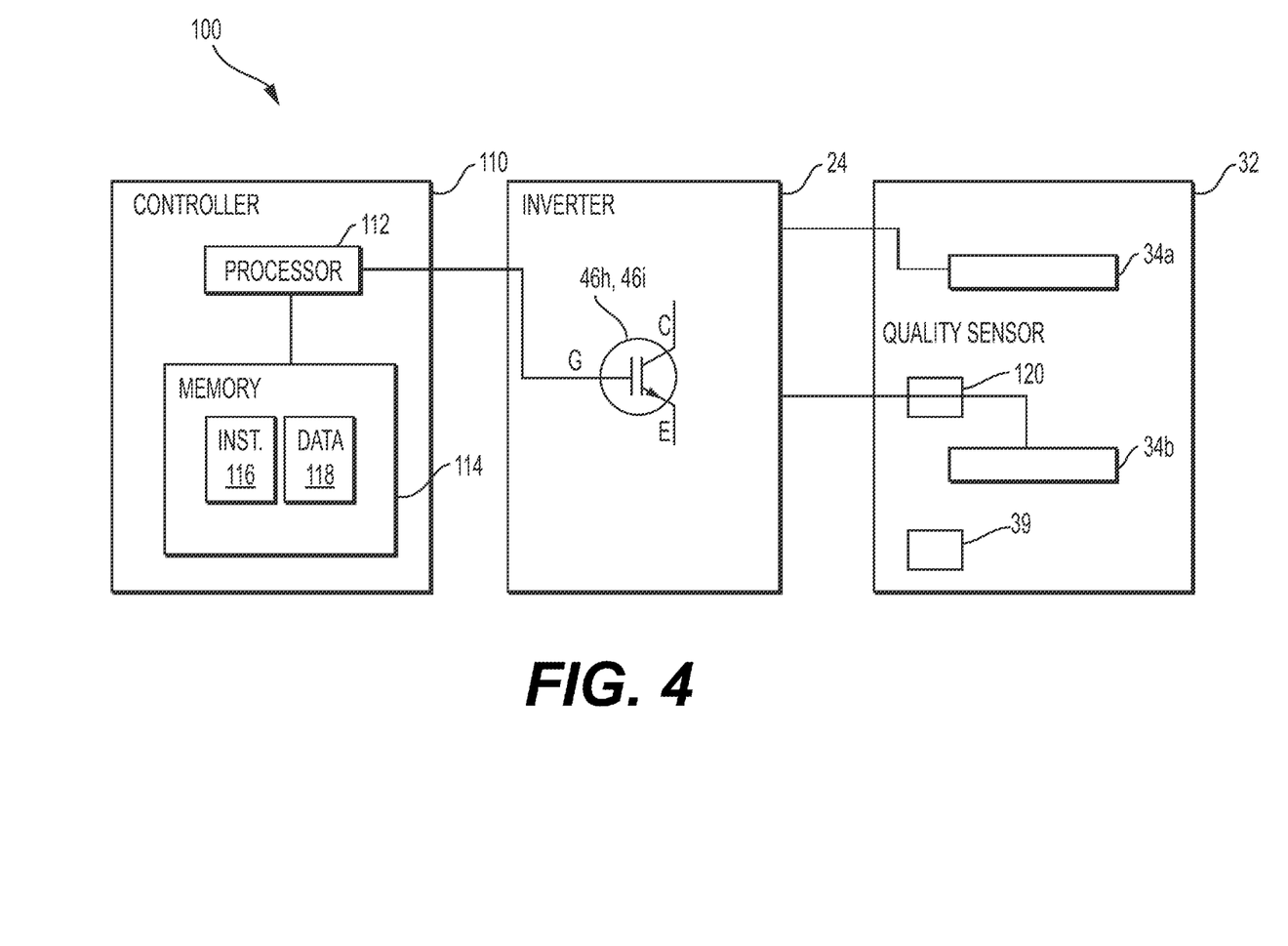
FIG. 4 shows a schematic block diagram of a monitoring system for detecting contamination in the lubricant/coolant fluid.

FIG. 4 shows a schematic block diagram of a monitoring system 100 for detecting contamination in the shared lubricant/coolant fluid. The monitoring system 100 includes a controller 110 for controlling various functions. The controller 110 may control operation of the inverter 24. For example, the controller 110 may generate a gate control signal for controlling operation of each of the high-side power switches 46h and the low-side power switches 46l of the inverter 24. The controller 110 may control operation of the inverter 24 for applying the AC excitation to the first plate 34a of the lubricant quality sensor 32. The lubricant quality sensor 32 also includes an electrical sensor 120 configured to measure an electrical response to the application of the AC excitation. The electrical sensor 120 may include a current sensor configured to measure electrical current in a conductor attached to one of the sensor plates 34a, 34b. Such a current sensor may, thereby, measure current between the sensor plates 34a, 34b. For example, and as shown in FIG. 4, the electrical sensor 120 is configured to measure electrical current in a conductor between the midpoint node and the second plate 34b of the lubricant quality sensor 32, i.e. the reference plate. Additionally or alternatively, the electrical sensor 120 may include other types of sensing devices, such as a voltage sensor and/or a sensor configured to detect an induced magnetic field.

In some embodiments, the electrical sensor 120 may be disposed on a printed circuit board (PCB) of the inverter 24 on which some or all of the power switches 46h, 46l of the inverter 24 are located.

According to a further aspect of the disclosure, the lubricant/coolant fluid 18 in the reservoir 38 is heated to a predetermined temperature (such as greater than 90 degrees Celsius) which results in the water present in the lubricant/coolant fluid 18 evaporating off to an environment of the reservoir 38. This heating process can occur during normal operation if the motor is operated in an inefficient manner, which results in an increase in the shared lubricant/coolant fluid temperature to the desired limit. This heating step would preferably coincide with an opening of a vent on the reservoir 38, which releases the resultant water vapor to the outside environment, but doesn't allow contaminants to enter the reservoir 38. This venting to the atmosphere could also be achieved with a screen and vent which do not need to be actuated, without departing from the scope of the subject disclosure. According to an aspect, the heating of the lubricant/coolant fluid 18 can be achieved by, or augmented by, increased switching frequency of the switches 46h, 46l of the inverter 24.

According to a further aspect of the disclosure, and as shown in FIG. 1, the lubricant quality sensor 32 could also include thermal spectroscopy sensor 39 configured to detect foaming in the lubricant/coolant fluid 18. This addition would result in a lubricant quality sensor 32 which could detect not only for the presence of metal and oil contaminants, but also foaming in the lubricant/coolant fluid 18.

The controller 110 may be operably connected to the electrical sensor 120 to receive a sensor signal indicative of the electrical current between the sensor plates 34a, 34b and in response to the AC excitation applied thereto. In some embodiments, the controller 110 may be operably connected to the thermal spectroscopy sensor 39 for receiving a signal therefrom indicative of foaming in the lubricant/coolant fluid 18. In some embodiments, the controller 110 may be operably connected to the inverter 24 for controlling operation of the phase drivers 42a, 42b, 42c for supplying AC current to the windings of the lubricant supported electric motor 11.

In some embodiments, the controller 110 may control may control other functions and/or components within the common lubrication, cooling and quality diagnostics system 10, such by measuring one or more temperatures and/or pressures of the shared lubricant/coolant fluid and/or by controlling operation of other components, such as the pump 36. The controller 110 includes a processor 112 coupled to a storage memory 114. The storage memory 114 includes an instruction storage 116 for storing instructions, such as program code for execution by the processor 112. The storage memory 114 also includes a data storage 118 for holding data for use by the processor 112. The data storage 118 may record, for example, values of parameters measured by one or more sensors, such as the lubricant quality sensor 32, and/or the outcome of functions calculated by the processor 112.

The controller 110 is configured to cause the inverter 24 to apply a plurality of AC frequencies to the sensor plates 34a, 34b at a fixed voltage, such that a current which flows between the sensor plates 34a, 34b is used to determine a complex impedance of the lubricant/coolant fluid 18 passing through the inverter passageway 26. From this complex impedance, a presence of water or metal contaminants in the lubricant/coolant fluid 18 can be determined. Accordingly, the lubricant quality sensor 32 utilizes existing high voltage as the excitation to perform a high-frequency sweep of the lubricant/coolant fluid 18 to detect for the presence of metal and water contaminants. This high-frequency sweep can flexibly be performed at vehicle start-up, while the vehicle is running, or after the vehicle has been shut down. The lubricant quality sensor 32 also advantageously makes an additional use of the high voltage which is already present in the electric powertrain to sense for major contaminants in the lubricant/coolant fluid 18, and thus reduces the number of additional components required to perform diagnostic measurements on the lubricant/coolant fluid 18 as compared to the prior art systems.

The controller 110 is configured to compare the amplitude and phase of a current measured by the electrical sensor 120 with the amplitude and phase of the exciting frequency and to thereby determine a complex impedance of the overall structure, with note that the resulting impedance is determined principally by characteristics of the lubricant/coolant fluid 18 and any contaminants therein.

In some embodiments, the system 10 is configured to determine the complex frequency by sweeping the excitation source to apply a range of different AC frequencies to the set of sensor plates 34a, 34b. Alternatively or additionally, the system 10 may be configured to determine the impedance of the lubricant/coolant fluid 18 during normal operation of the inverter 24 when the desired excitation frequencies occur without explicit programming. To assist in use of a normal inverter operating mode as a means to excite the lubricant/coolant fluid 18 plus contaminants, at least one additional plate 34c may be disposed closer or further away from the first plate 34a. This may affect sensitivity of the impedance observer algorithm in certain modes where contaminants are more difficult to determine in the lubricant/coolant fluid 18. This may also be advantageous when the frequency is swept as part of an off-line diagnostic test and the inverter 24 is not driving the lubricant supported electric motor 11.

As will be appreciated in view of the above-mentioned disclosure, the use of impedance measurements on the lubricant/coolant fluid 18 is significantly more advanced than any techniques used today for ICEs. Additionally, the lubricant quality sensor 32 is more sophisticated that prior art mechanisms for detecting for the presence of contaminants, and advantageously addresses the full spectrum of the contamination problem in fluids and oils—not just the problem of metal contaminants.

Figure 5:
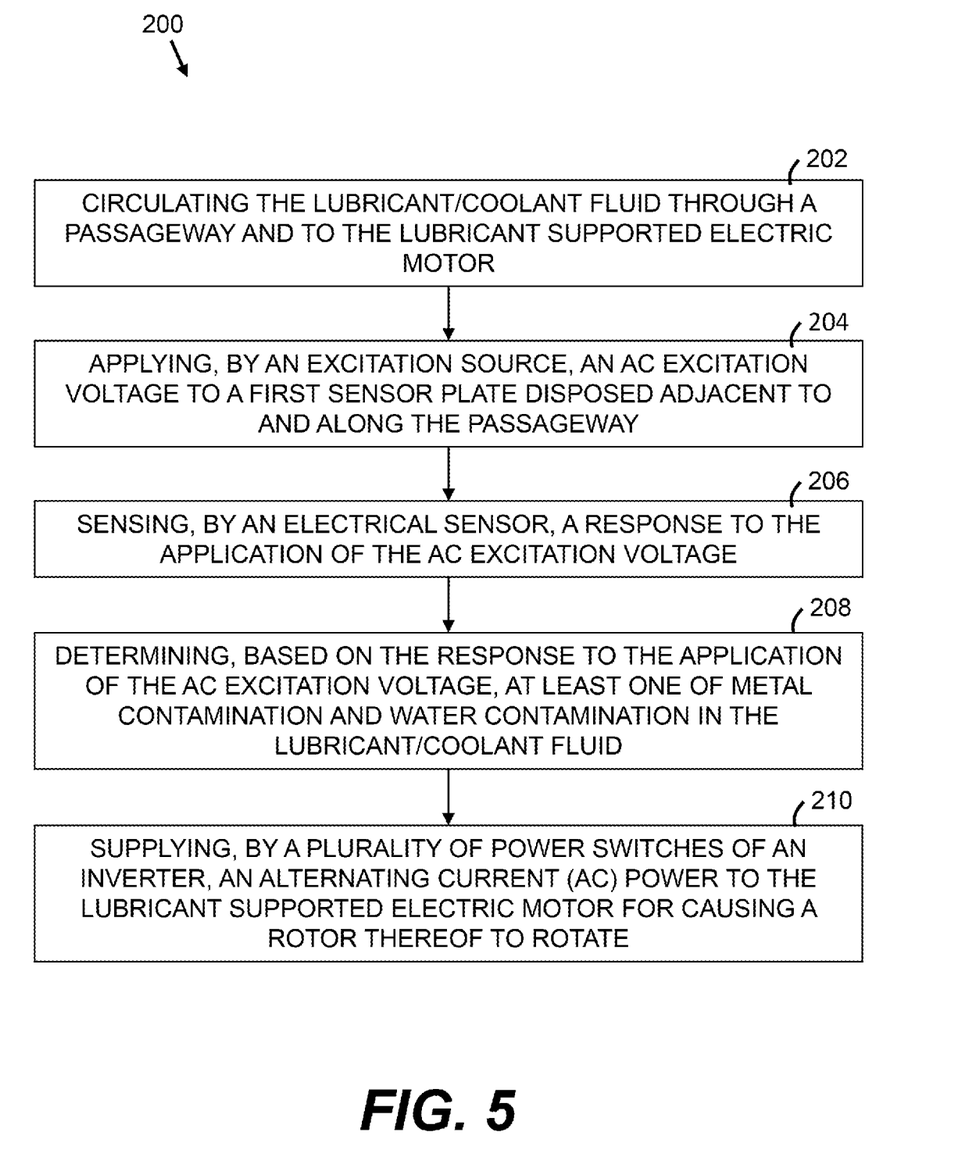
FIG. 5 shows a flow chart illustrating steps in a method for sensing contaminants in a lubricant/coolant fluid of a lubricant supported electric motor, in accordance with an aspect of the present disclosure.

FIG. 5 shows a flow chart illustrating steps in a method 200 for sensing contaminants in a lubricant/coolant fluid of a lubricant supported electric motor. As can be appreciated in light of the disclosure, the order of operation within the method 200 is not limited to the sequential execution as illustrated in FIG. 5, but may be performed in one or more varying orders as applicable and in accordance with the present disclosure.

The method 200 includes circulating the lubricant/coolant fluid through a passageway and to the lubricant supported electric motor at step 202.

The method 200 also includes applying, by an excitation source, an AC excitation voltage to a first sensor plate disposed adjacent to and along the passageway at step 204.

In some embodiments, step 204 further includes applying a predetermined range of AC frequencies to the first sensor plate to generate an electric field in the lubricant/coolant fluid, and where the predetermined range of AC frequencies is selected to generate a corresponding response to an interaction between the electric field and the at least one of metal contamination and water contamination in the lubricant/coolant fluid. In some embodiments, the predetermined range of AC frequencies are substantially higher than a frequency of the AC power applied to the lubricant supported electric motor for driving the rotor to rotate.

The method 200 also includes sensing, by an electrical sensor, a response to the application of the AC excitation voltage at step 206. For example, the electrical sensor 120 may sense an electrical current having a particular frequency and/or phase as the response to the application of the AC excitation voltage.

The method 200 also includes determining, based on the response to the application of the AC excitation voltage, at least one of metal contamination and water contamination in the lubricant/coolant fluid at step 208.

In some embodiments, step 208 includes comparing at least one of an amplitude and a phase of the response measured by the sensor with a corresponding one of an amplitude and a phase of the AC excitation voltage. For example, the processor 112 may execute program instructions to compare the amplitude and/or the phase of the response measured by the sensor with the corresponding amplitude and/or the phase of the AC excitation voltage.

The method 200 also includes supplying, by a plurality of power switches of an inverter, an alternating current (AC) power to the lubricant supported electric motor for causing a rotor thereof to rotate at step 210. In some embodiments, step 204 includes the plurality of power switches of the inverter also functioning as the excitation source to apply the AC excitation voltage to the first sensor plate.

A quality diagnostics system for lubricant/coolant fluid includes a lubricant supported electric motor including a stator and a rotor defining a gap therebetween, with the lubricant/coolant fluid disposed in the gap for supporting the rotor while allowing the rotor to rotate relative to the stator. The system also includes an inverter including a plurality of power switches configured to supply an alternating current (AC) power to the lubricant supported electric motor for driving the rotor to rotate. The system also includes a passageway configured to convey the lubricant/coolant fluid between the lubricant supported electric motor and the inverter. The system also includes a lubricant quality sensor including a set of sensor plates disposed along the passageway, an excitation source configured to apply an AC excitation voltage to a first sensor plate of the set of sensor plates, and an electrical sensor configured to measure a response to the AC excitation voltage.

In some embodiments, the set of sensor plates includes two sensor plates disposed on opposite sides of the passageway.

In some embodiments, the set of sensor plates are disposed within an enclosure of the inverter.

In some embodiments, the set of sensor plates includes a reference plate having a reference voltage.

In some embodiments, the inverter includes a DC positive conductor and a DC negative conductor and series combination of input capacitors connected therebetween to define a midpoint node, and wherein the reference plate is connected to the midpoint node.

In some embodiments, the electrical sensor is configured to measure an electrical current in a conductor attached to one of the sensor plates.

In some embodiments, the inverter includes a printed circuit board with the plurality of power switches and the electrical sensor disposed thereupon.

In some embodiments, the plurality of power switches in the inverter are further configured to function as the excitation source for applying the AC excitation to the first sensor plate of the set of sensor plates.

In some embodiments, the system further includes a controller configured to cause the excitation source to apply the AC excitation voltage to the first sensor plate and to receive a sensor signal from the electrical sensor indicative of the response to the application of the AC excitation voltage. In some embodiments, the controller is further configured to determine, based on the sensor signal, at least one of metal contamination and water contamination in the lubricant/coolant fluid.

In some embodiments, the causing the excitation source to apply the AC excitation voltage to the first sensor plate includes the controller commanding the excitation source to apply a predetermined range of AC frequencies to the first sensor plate to generate an electric field in the lubricant/coolant fluid between the set of sensor plates, the predetermined range of AC frequencies configured to generate a corresponding response to an interaction between the electric field and the at least one of metal contamination and water contamination in the lubricant/coolant fluid.

In some embodiments, the predetermined range of AC frequencies are substantially higher than a frequency of the AC power applied to the lubricant supported electric motor for driving the rotor to rotate.

In some embodiments, determining the least one of metal contamination and water contamination in the lubricant/coolant fluid further includes the controller being configured to compare at least one of an amplitude and a phase of the sensor signal with a corresponding one of an amplitude and a phase of the AC excitation voltage.

In some embodiments, the lubricant quality sensor further includes a thermal spectroscopy sensor configured to detect foaming in the lubricant/coolant fluid.

A quality diagnostics system for lubricant/coolant fluid of a vehicle includes a lubricant supported electric motor including a stator and a rotor defining a gap therebetween, with a lubricant/coolant fluid disposed in the gap for supporting the rotor while allowing the rotor to rotate relative to the stator. The system also includes a passageway configured to convey the lubricant/coolant fluid between the lubricant supported electric motor and one or more other components. The system also includes a lubricant quality sensor including a set of sensor plates disposed along the passageway and an excitation source configured to supply an AC excitation voltage to at least one sensor plate of the set of sensor plates. The system also includes a controller configured to cause the excitation source to apply the AC excitation voltage to the at least one sensor plate. The system also includes an electrical sensor configured to measure an electrical response to the application of the AC excitation voltage. The controller is further configured to determine, based on a sensor signal from the electrical sensor, at least one of metal contamination and water contamination in the lubricant/coolant fluid.

In some embodiments, the controller is configured to apply the AC excitation voltage to the at least one sensor plate during at least one of a vehicle startup and a vehicle shutdown.

A method for sensing contaminants in a lubricant/coolant fluid of a lubricant supported electric motor includes: circulating the lubricant/coolant fluid through a passageway and to the lubricant supported electric motor; applying, by an excitation source, an AC excitation voltage to a first sensor plate disposed adjacent to and along the passageway; sensing, by an electrical sensor, a response to the application of the AC excitation voltage; and determining, based on the response to the application of the AC excitation voltage, at least one of metal contamination and water contamination in the lubricant/coolant fluid.

In some embodiments, the method further includes supplying, by a plurality of power switches of an inverter, an alternating current (AC) power to the lubricant supported electric motor for causing a rotor thereof to rotate. In some embodiments, the plurality of power switches of the inverter also function as the excitation source to apply the AC excitation voltage to the first sensor plate.

In some embodiments, applying the AC excitation voltage further includes applying a predetermined range of AC frequencies to the first sensor plate to generate an electric field in the lubricant/coolant fluid, the predetermined range of AC frequencies configured to generate a corresponding response to an interaction between the electric field and the at least one of metal contamination and water contamination in the lubricant/coolant fluid.

In some embodiments, the predetermined range of AC frequencies are substantially higher than a frequency of the AC power applied to the lubricant supported electric motor for driving the rotor to rotate.

In some embodiments, determining the at least one of metal contamination and water contamination in the lubricant/coolant fluid further includes comparing at least one of an amplitude and a phase of the response measured by the sensor with a corresponding one of an amplitude and a phase of the AC excitation voltage.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A quality diagnostics system for lubricant/coolant fluid, comprising:
   a lubricant supported electric motor including a stator and a rotor defining a gap therebetween, with the lubricant/coolant fluid disposed in the gap for supporting the rotor while allowing the rotor to rotate relative to the stator;

an inverter including a plurality of power switches configured to supply an alternating current (AC) power to the lubricant supported electric motor for driving the rotor to rotate;

a passageway configured to convey the lubricant/coolant fluid between the lubricant supported electric motor and the inverter;

a lubricant quality sensor including a set of sensor plates disposed along the passageway, an excitation source configured to apply an AC excitation voltage to a first sensor plate of the set of sensor plates, and an electrical sensor configured to measure a response to the AC excitation voltage; and the plurality of power switches in the inverter further configured to function as the excitation source for applying the AC excitation to the first sensor plate of the set of sensor plates.

2. The system of claim 1, wherein the set of sensor plates includes two sensor plates disposed on opposite sides of the passageway.

3. The system of claim 1, wherein the set of sensor plates are disposed within an enclosure of the inverter.

4. The system of claim 1, wherein the set of sensor plates includes a reference plate having a reference voltage.

5. The system of claim 1, wherein the electrical sensor is configured to measure an electrical current in a conductor attached to one of the sensor plates.

6. The system of claim 1, further comprising a controller configured to cause the excitation source to apply the AC excitation voltage to the first sensor plate and to receive a sensor signal from the electrical sensor indicative of the response to the application of the AC excitation voltage; and wherein the controller is further configured to determine, based on the sensor signal, at least one of metal contamination and water contamination in the lubricant/coolant fluid.

7. The system of claim 6, wherein causing the excitation source to apply the AC excitation voltage to the first sensor plate includes the controller commanding the excitation source to apply a predetermined range of AC frequencies to the first sensor plate to generate an electric field in the lubricant/coolant fluid between the set of sensor plates, the predetermined range of AC frequencies configured to generate a corresponding response to an interaction between the electric field and the at least one of metal contamination and water contamination in the lubricant/coolant fluid.

8. The system of claim 7, wherein the predetermined range of AC frequencies are higher than a frequency of the AC power applied to the lubricant supported electric motor for driving the rotor to rotate.

9. The system of claim 6, wherein determining the least one of metal contamination and water contamination in the lubricant/coolant fluid further includes the controller being configured to compare at least one of an amplitude and a phase of the sensor signal with a corresponding one of an amplitude and a phase of the AC excitation voltage.

10. The system of claim 1, wherein the lubricant quality sensor further includes a thermal spectroscopy sensor configured to detect foaming in the lubricant/coolant fluid.

11. A quality diagnostics system for lubricant/coolant fluid, comprising:

a lubricant supported electric motor including a stator and a rotor defining a gap therebetween, with the lubricant/coolant fluid disposed in the gap for supporting the rotor while allowing the rotor to rotate relative to the stator;

an inverter including a plurality of power switches configured to supply an alternating current (AC) power to the lubricant supported electric motor for driving the rotor to rotate;

a passageway configured to convey the lubricant/coolant fluid between the lubricant supported electric motor and the inverter;

a lubricant quality sensor including a set of sensor plates disposed along the passageway, an excitation source configured to apply an AC excitation voltage to a first sensor plate of the set of sensor plates, and an electrical sensor configured to measure a response to the AC excitation voltage;

the set of sensor plates including a reference plate having a reference voltage; and wherein the inverter includes a DC positive conductor and a DC negative conductor and series combination of input capacitors connected therebetween to define a midpoint node, and wherein the reference plate is connected to the midpoint node.

12. A quality diagnostics system for lubricant/coolant fluid, comprising:

a lubricant supported electric motor including a stator and a rotor defining a gap therebetween, with the lubricant/coolant fluid disposed in the gap for supporting the rotor while allowing the rotor to rotate relative to the stator;

an inverter including a plurality of power switches configured to supply an alternating current (AC) power to the lubricant supported electric motor for driving the rotor to rotate;

a passageway configured to convey the lubricant/coolant fluid between the lubricant supported electric motor and the inverter;

a lubricant quality sensor including a set of sensor plates disposed along the passageway, an excitation source configured to apply an AC excitation voltage to a first sensor plate of the set of sensor plates, and an electrical sensor configured to measure a response to the AC excitation voltage;

wherein the electrical sensor is configured to measure an electrical current in a conductor attached to one of the sensor plates; and wherein the inverter includes a printed circuit board with the plurality of power switches and the electrical sensor disposed thereupon.

13. A quality diagnostics system for lubricant/coolant fluid in a vehicle, comprising:

a lubricant supported electric motor including a stator and a rotor defining a gap therebetween, with the lubricant/coolant fluid disposed in the gap for supporting the rotor while allowing the rotor to rotate relative to the stator;

a passageway configured to convey the lubricant/coolant fluid between the lubricant supported electric motor and one or more other components;

a lubricant quality sensor including a set of sensor plates disposed along the passageway and an excitation source configured to supply an AC excitation voltage to at least one sensor plate of the set of sensor plates;

a controller configured to cause the excitation source to apply the AC excitation voltage to the at least one sensor plate;

an electrical sensor configured to measure an electrical response to the application of the AC excitation voltage; and the controller further configured to determine, based on a sensor signal from the electrical sensor, at least one of metal contamination and water contamination in the lubricant/coolant fluid; and an inverter including a plurality of power switches configured to supply an alternating current power to the lubricant supported electric motor for driving the rotor to rotate, and wherein the plurality of power switches in the inverter are further configured to function as the excitation source for applying the AC excitation to the at least one sensor plate of the set of sensor plates.

14. The system of claim 13, wherein the controller is configured to apply the AC excitation voltage to the at least one sensor plate during at least one of a vehicle startup and a vehicle shutdown.

15. A method for sensing contaminants in a lubricant/coolant fluid of a lubricant supported electric motor, comprising:

circulating the lubricant/coolant fluid through a passageway and to the lubricant supported electric motor;

applying, by an excitation source, an AC excitation voltage to a first sensor plate disposed adjacent to and along the passageway; and sensing, by an electrical sensor, a response to the application of the AC excitation voltage;

determining, based on the response to the application of the AC excitation voltage, at least one of metal contamination and water contamination in the lubricant/coolant fluid; and supplying, by a plurality of power switches of an inverter, an alternating current (AC) power to the lubricant supported electric motor for causing a rotor thereof to rotate, and wherein the plurality of power switches of the inverter also function as the excitation source to apply the AC excitation voltage to the first sensor plate.

16. The method of claim 15, wherein applying the AC excitation voltage further includes applying a predetermined range of AC frequencies to the first sensor plate to generate an electric field in the lubricant/coolant fluid, the predetermined range of AC frequencies configured to generate a corresponding response to an interaction between the electric field and the at least one of metal contamination and water contamination in the lubricant/coolant fluid.

17. The method of claim 16, wherein the predetermined range of AC frequencies are higher than a frequency of the AC power applied to the lubricant supported electric motor for driving the rotor to rotate.

18. The method of claim 15, wherein determining the at least one of metal contamination and water contamination in the lubricant/coolant fluid further includes comparing at least one of an amplitude and a phase of the response measured by the sensor with a corresponding one of an amplitude and a phase of the AC excitation voltage.

* * * * *